United States Patent
Urbaniak et al.

(10) Patent No.: US 9,597,227 B2
(45) Date of Patent: Mar. 21, 2017

(54) TRANS-SCLERA PORTAL FOR DELIVERY OF THERAPEUTIC AGENTS

(71) Applicant: Abbott Medical Optics Inc., Santa Ana, CA (US)

(72) Inventors: Daniel J. Urbaniak, Aliso Viejo, CA (US); John J. Stankus, Campbell, CA (US); James Su, San Bruno, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 82 days.

(21) Appl. No.: 13/837,892

(22) Filed: Mar. 15, 2013

(65) Prior Publication Data

US 2014/0276329 A1     Sep. 18, 2014

(51) Int. Cl.
| | | |
|---|---|---|
| *A61F 9/00* | (2006.01) | |
| *A61F 9/007* | (2006.01) | |
| *A61M 39/02* | (2006.01) | |
| *A61K 9/00* | (2006.01) | |

(52) U.S. Cl.
CPC .......... *A61F 9/0017* (2013.01); *A61F 9/0008* (2013.01); *A61F 2210/0061* (2013.01); *A61F 2250/0067* (2013.01); *A61F 2250/0068* (2013.01); *A61K 9/0004* (2013.01); *A61K 9/0051* (2013.01); *A61M 2039/0276* (2013.01); *A61M 2210/0612* (2013.01)

(58) Field of Classification Search
CPC .............. A61F 9/007; A61F 2250/0067; A61F 2250/0068; A61F 2250/0069; A61F 9/0008; A61F 9/0026; A61M 2210/0612; A61M 5/14244; A61M 5/14276; A61M 5/1428; A61M 2005/14284; A61M 2039/1072; A61M 39/0208; A61M 2039/0226; A61K 9/0051; A61K 9/0024; B32B 2307/762; B32B 27/18; B32B 27/26; B32B 2037/1253; C08F 2500/21; B29C 73/16; B29C 73/22
See application file for complete search history.

(56) References Cited

U.S. PATENT DOCUMENTS

| | | | | |
|---|---|---|---|---|
| 4,455,144 A | * | 6/1984 | Michaels | A61M 31/002 604/892.1 |
| 4,634,427 A | * | 1/1987 | Hannula | A61M 5/1428 604/185 |
| 4,781,675 A | * | 11/1988 | White | 604/10 |
| 5,092,849 A | * | 3/1992 | Sampson | A61M 39/0208 604/175 |
| 5,466,233 A | * | 11/1995 | Weiner et al. | 604/890.1 |

(Continued)

FOREIGN PATENT DOCUMENTS

| | | | | |
|---|---|---|---|---|
| AT | 395678 B | * | 2/1993 | ........ A61M 39/0208 |
| EP | 1640450 A1 | | 3/2006 | |

(Continued)

OTHER PUBLICATIONS

Google translate Tue Mar. 1, 2016 of AT 395678.*

(Continued)

*Primary Examiner* — Adam Marcetich
(74) *Attorney, Agent, or Firm* — Abbott Medical Optics Inc.

(57) ABSTRACT

A portal through the sclera for delivery of an effective amount of therapeutic agent to the back of the eye.

22 Claims, 6 Drawing Sheets

(56) References Cited

U.S. PATENT DOCUMENTS

| | | | |
|---|---|---|---|
| 5,704,915 A * | 1/1998 | Melsky | A61M 39/0208 604/175 |
| 5,725,493 A * | 3/1998 | Avery et al. | 604/9 |
| 5,830,173 A * | 11/1998 | Avery et al. | 604/9 |
| 6,251,090 B1 * | 6/2001 | Avery et al. | 604/9 |
| 8,440,216 B2 | 5/2013 | Huang et al. | |
| 2003/0047011 A1 * | 3/2003 | Diermann | A61B 5/1405 73/864.02 |
| 2004/0106906 A1 * | 6/2004 | Yaacobi | 604/294 |
| 2004/0230183 A1 * | 11/2004 | Breegi | A61F 9/0017 604/891.1 |
| 2005/0197636 A1 * | 9/2005 | Halili | A61M 5/14276 604/288.01 |
| 2005/0255144 A1 | 11/2005 | Schultz | |
| 2006/0067978 A1 * | 3/2006 | Heiler | A61K 9/0051 424/427 |
| 2006/0200097 A1 * | 9/2006 | Humayun et al. | 604/288.01 |
| 2006/0258994 A1 | 11/2006 | Avery | |
| 2007/0095158 A1 * | 5/2007 | Maeda | G01N 35/1095 73/864 |
| 2007/0191863 A1 | 8/2007 | De Juan, Jr. et al. | |
| 2007/0298075 A1 * | 12/2007 | Borgia | A61F 9/0017 424/428 |
| 2008/0113935 A1 | 5/2008 | Yedgar et al. | |
| 2008/0161741 A1 * | 7/2008 | Bene et al. | 604/9 |
| 2008/0167600 A1 * | 7/2008 | Peyman | 604/20 |
| 2008/0277332 A1 * | 11/2008 | Liu | 210/500.22 |
| 2008/0318843 A1 | 12/2008 | Schultz et al. | |
| 2009/0062417 A1 * | 3/2009 | Wrobel et al. | 522/66 |
| 2009/0191402 A1 * | 7/2009 | Beiermann et al. | 428/323 |
| 2009/0220572 A1 | 9/2009 | Deschatelets et al. | |
| 2010/0051575 A1 * | 3/2010 | Ou et al. | 215/247 |
| 2010/0063461 A1 * | 3/2010 | Esteve | A61M 39/0208 604/288.02 |
| 2010/0174272 A1 * | 7/2010 | Weiner | A61F 9/0017 604/891.1 |
| 2010/0331880 A1 * | 12/2010 | Stopek | 606/219 |
| 2011/0052678 A1 | 3/2011 | Shantha et al. | |
| 2011/0288525 A1 * | 11/2011 | Hallen et al. | 604/506 |
| 2013/0085473 A1 * | 4/2013 | Weilbacher | A61M 39/00 604/513 |
| 2013/0165860 A1 * | 6/2013 | Doud et al. | 604/117 |
| 2013/0309412 A1 * | 11/2013 | Toub et al. | 427/515 |
| 2013/0324918 A1 * | 12/2013 | de Juan et al. | 604/36 |
| 2015/0080846 A1 * | 3/2015 | de Juan et al. | 604/506 |

FOREIGN PATENT DOCUMENTS

| | | |
|---|---|---|
| WO | WO-0064393 A1 | 11/2000 |
| WO | WO-02100318 A2 | 12/2002 |
| WO | 2007084582 A2 | 7/2007 |
| WO | 2009032266 A2 | 3/2009 |
| WO | WO-2010088548 A1 | 8/2010 |

OTHER PUBLICATIONS

International Search Report and Written Opinion for Application No. PCT/US2014/018531, mailed Aug. 26, 2014, 23 pages.
European Search Report for Application No. EP16170597, mailed on Nov. 8, 2016, 8 pages.

* cited by examiner

TRANS-SCLERA PORTAL FOR DELIVERY OF THERAPEUTIC AGENTS

FIELD OF THE INVENTION

The instant disclosure relates to the delivery of pharmaceuticals and the like to the back of the eye and, more particularly, to a portal through the sclera for delivery of an effective amount of therapeutic agent to the back of the eye.

BACKGROUND

There are three primary structures within the human eye that are essential to vision and subject to age-related damage: the cornea, lens and retina. The retina is a multi-layered sensory tissue that lines the back of the eye. It contains millions of photoreceptors that capture light rays and convert them into electrical impulses. These impulses travel along the optic nerve to the brain where they are turned into images. There are two types of photoreceptors in the retina: rods and cones. The retina contains approximately 6 million cones. The cones are contained in the macula, the portion of the retina responsible for central vision. They are most densely packed within the fovea, the very center portion of the macula. Cones function best in bright light and allow us to appreciate color. There are approximately 125 million rods. They are spread throughout the peripheral retina and function best in dim lighting. The rods are responsible for peripheral and night vision. The retina is essential for vision and is easily damaged by prolonged unprotected exposure to visible and near visible light. Light-induced retinal pathologies include cystoid macular oedema, solar retinopathy, ocular melanomas and age-related macular degeneration (ARMD). Light-induced retinal damage is classified as structural, thermal or photochemical and is largely determined by the exposure time, power level and wavelength of light.

In healthy adults the retina is generally protected from the most severe forms of light-induced damage by the outer eye structures, including the cornea and crystalline lens. The cornea is a transparent proteinaceous ocular tissue located in front of the iris and is the only transparent eye structure exposed directly to the external environment. The cornea is essential for protecting the delicate internal structures from damage and facilitates the transmission of light through the aqueous humor to the crystalline lens.

The crystalline lens is an accommodating biological lens lying in back of the cornea, anterior chamber filled with aqueous humor, and the iris. Between the lens and the retina is the vitreous chamber filled with vitreous humor. The optical pathway through the eye acts to refract the light entering the eye, with the cornea providing most of the optical power, and the accommodating lens facilitating the convergence of both far and near images onto the retina. Ocular elements in the optical pathway absorb various wavelengths of light, while permitting others to pass through. In the normal human eye, only wavelengths of light between about 400 nm and 1,400 nm can pass through the refracting elements of the eye to the retina. However, high transmittance levels of blue and violet light (wavelengths from about 390 nm to about 500 nm) has been linked to conditions such as retinal damage, macular degeneration, retinitis pigmentosa, and night blindness.

Intraocular pressure (IOP) in the eye can significantly affect the elements of the ocular pathway, and is maintained by the formation and drainage of aqueous humor, a clear, colorless fluid that fills the anterior and posterior chambers of the eye. Aqueous humor normally flows from the anterior chamber of the eye out through an aqueous outflow channel at a rate of 2 to 3 microliters per minute.

Glaucoma, for example, is a progressive disease of the eye characterized by a gradual loss of nerve axons at the optic nerve head. In many cases, the damage to the optic nerve head is due to increased intraocular pressure. This increase in pressure is most commonly caused by stenosis or blockage of the aqueous outflow channel, resulting in excessive buildup of aqueous fluid within the eye. Other causes include increase in venous pressure outside the eye which is reflected back through the aqueous drainage channels and increased production of aqueous humor. In a "normal" eye, IOP ranges from 8 to 21 mm mercury. In an eye with glaucoma, IOP can range between normal pressures up to as much as 50 mm mercury. This increase in IOP produces gradual and permanent loss of vision in the afflicted eye.

Existing corrective methods for the treatment of glaucoma include drugs, surgery, and implants. In many cases therapy can require delivery of various therapeutic agents to various portions of the eye over a lengthy period of time, typically by injection of the agent directly into the eye.

There are numerous examples of surgical procedures that have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous humor free passage from the posterior to the anterior chambers in the eye. A trabeculotomy, opening the inner wall of Schlemm's canal, is often performed in cases of developmental or juvenile glaucoma so as to increase the outflow of the aqueous humor, thereby decreasing IOP. In adults, a trabeculectomy shunts fluid through a trapdoor flap in the eye that performs a valve-like function for the first few weeks after surgery.

While often successful, these surgical techniques possess inherent risks associated with invasive surgery on an already afflicted or compromised eye. Furthermore, the tissue of the eye can scar over this small area and the eye reverts to the pre-operative condition, thereby necessitating the need for further treatment.

Ocular implants are sometimes used in long-term glaucoma treatment. One early implant is called the Molteno Implant, after A. C. B. Molteno. The implant is a small circular plate with a rigid translimbal drainage tube attached. The plate was 8.5 mm in diameter and formed a surface area of about 100 mm². This implant is sutured to the sclera in the anterior segment of the eye near the limbus and the drainage tube is inserted into the anterior chamber of the eye. Once implanted, the body forms scar tissue around the plate. Fluid causes the tissue above the plate to lift and form a bleb into which aqueous humor flows from the anterior chamber via the drainage tube. A bleb is a fluid filled space surrounded by scar tissue, somewhat akin to a blister. The fluid within the bleb then flows through the scar tissue, at a rate which can regulate IOP.

A newer implant has been redesigned for insertion into the posterior segment of the eye to avoid problems with early designs. This implant is referred to as a long tube Molteno implant. The implant comprises a flexible drainage tube connected to one or more rigid plate reservoirs. The plates are shaped to conform to the curvature of the eye. The reservoir plate is placed under Tenon's capsule in the posterior segment of the eye and sutured to the sclera. The drainage tube is implanted into the anterior chamber through a scleral incision. However, the long tube Molteno implant is still disadvantageous, as the plates are formed of a rigid plastic which makes insertion beneath the eye tissue difficult and time-consuming.

After such an implant is attached, IOP tends to fall as aqueous fluid flows immediately through the drainage tube. However, an open drainage tube may release too much of the fluid too fast, which is detrimental to the eye. It is not until 2-6 weeks later that the bleb forms around the plate to sufficiently regulate the fluid flow. Some prior devices have therefore incorporated valves in the fluid drain path designed to function for a limited time until the bleb forms. However, such valved devices sometimes clog later, requiring another surgery.

More recently introduced implants feature a flexible plate that attaches to the sclera, and a drainage tube positioned for insertion into the anterior chamber of the eye. A bleb forms around the plate and fluid drains into and out of the bleb to regulate IOP. This type of shunt is called a Baerveldt shunt. One such device has an open tube with no flow restricting elements. Temporary sutures are used to restrict fluid flow for a predetermined period after which the bleb forms and fluid drainage is properly regulated. The temporary sutures are either biodegradable or removed in a separate procedure. This method works well, but the timing of suture dissolution is inexact and may operate improperly, and a second procedure undesirable.

Some shunts also include fenestrations through the plate to promote fibrous adhesion, which may reduce bleb height. Though a bleb is thought to have a beneficial function in regulating aqueous humor diffusion, too large of a bleb may cause the patient some pain or may be aesthetically unacceptable. Some doctors even prefer to use anti-proliferatives such as mitomycin C or 5-FU at the time of surgery to prevent formation of the fibrous bleb. Another potential complication is endophthalmitis, an inflammation of the internal tissue of the eye. This complication may occur in any intraocular surgery, with possible loss of vision and even of the eye itself. Infectious etiology is the most common cause, and various bacteria and fungi have been isolated as the cause of the endophthalmitis. The risk of infection is more pronounced early in a shunt implant procedure, when a passage to the interior of the eye is created and fluid flows therethrough. Later, the bleb acts as a filter to prevent microorganisms such as bacteria from entering the eye.

Some eye diseases can be treated with pharmaceuticals. However, where the diseases primarily affect the back of the eye, it can be difficult to administer and achieve effective levels of therapeutic agents in that portion of the eye. Such diseases are typically treated by direct injection of biologically active pharmaceutical agents, such as anti-inflammatory steroids and target-specific antibodies. Treatment may entail repeated injections that can put the patient at risk of complications involving conditions such as infection, endophthalmitis, high intraocular pressure (IOP), glaucoma, cataract, retinal detachment and bleeding, and lack of wound-healing. A new approach is needed that can deliver pharmaceuticals and the like to the back of the eye while mitigating the adverse effects that attend the prior art. However, any solutions requiring patient compliance or repeated injection run the risk of failure due to noncompliance of the patient.

SUMMARY OF THE DISCLOSURE

An apparatus and method for delivery of an effective amount of therapeutic agent to the back of the eye via a portal through the sclera is disclosed. In an embodiment of the present invention, the portal comprises an implantable shunt for repeated injection of ophthalmic pharmaceutical treatments into an eye. The shunt and associated method may include a partition wall or septum configured to provide separation between the intraocular and intraorbital spaces of the eye. The wall may be re-sealable or self-healing after each injection.

The implantable shunt and associated method may also comprise a swell loadable polymeric ocular insert with a micron scale tab that, when inserted into the eye, may extend through the sclera into the intravitreal space as a transport channel. Such a tab may wick a therapeutic agent from the insert into the intravitreal space. It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical optical and surgical devices, systems, and methods. Those of ordinary skill may recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Figure 1A:
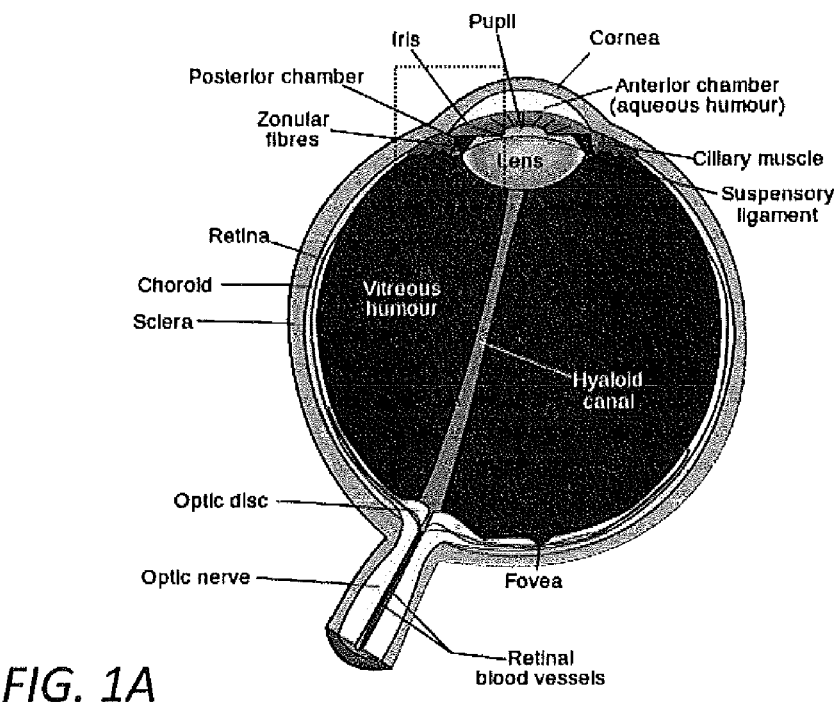
FIG. 1A illustrates a human eye in cross section.
Figure 1B:
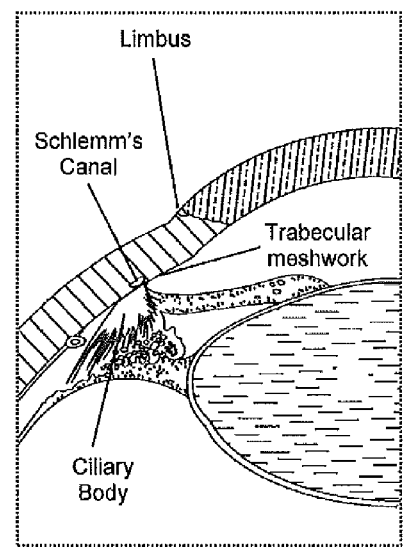
FIG. 1B illustrates in greater detail the portion of the eye of FIG. 1A enclosed in the dotted box.

FIG. 1A illustrates a human eye in cross section with the eye in an upward orientation relative to the page. FIG. 1B illustrates in greater detail the portion of the eye of FIG. 1A enclosed in the dotted box. The relevant structures of the eye are described briefly to provide background and context for anatomical terms incorporated herein. A number of anatomical details have been omitted for clarity.

Referring to FIG. 1A, the sclera is a tough outer membrane of the eye that covers most of the eye except the portion in the front of the eye, which is covered by the cornea. The sclera forms the posterior five-sixths or so of the connective tissue coat of the eyeball. It maintains the shape of the eyeball, and is resistant to internal and external forces. It also provides attachments for the extraocular muscle insertions. The choroid is a vascular layer lying adjacent to the inside surface of the sclera. It contains connective tissue to the sclera on the outside, and to the retina on the inside. The choroid provides oxygen and nourishment to the outer layers of the retina. The retina is a light-sensitive layer of tissue, adjacent to the choroid and lining the inner surface of the globe of the eye. The optics of the eye create an image of the field of vision on the retina, which initiates processes that ultimately trigger nerve impulses. The impulses are conveyed by the optic nerve to the visual centers of the brain.

The cornea is the transparent anterior (front) part of the eye that covers the iris, pupil, and anterior chamber. Light enters the eye through the cornea, proceeds through the aqueous humor in the anterior chamber, through the pupil, lens, and vitreous humor, and on to the retina. The cornea, lens, and humors refract the light to form the image on the retina, with the cornea accounting for approximately two-thirds of the eye's total optical power. The pupil is defined by an aperture in the iris, which is located in front of the lens.

The cornea merges into the sclera at a juncture called the limbus. The ciliary muscle and ciliary processes form the ciliary body, located near the limbus on the inside surface of the eye. Aqueous humor is secreted by the ciliary processes, and passes through the pupil into the anterior chamber, which is defined by the space between the iris and the cornea. In a healthy eye, the aqueous humor is absorbed through the trabecular meshwork, then proceeds through Schlemm's canal and on through veins which merge into venous blood circulation. Intraocular pressure (IOP) is maintained in the eye largely by the balance of secretion, absorption, and outflow of the aqueous humor through the mechanism described above.

The vitreous humor (or humour) is a clear gel that fills the space between the lens and the retina of the eye, called the vitreous chamber. Unlike the aqueous humor which is dynamic and continuously replenished, the vitreous humor is static and is not replenished. One common abnormal eye condition, glaucoma, is a disease in which the optic nerve at the back of the eye is damaged in a characteristic manner. Abnormally high fluid pressure in the aqueous humor in the anterior chamber is a significant risk factor for developing glaucoma. If left untreated, glaucoma can lead to permanent damage of the optic nerve and resultant visual field loss, which can progress to blindness.

Another condition, Macular Degeneration (MD), which may be Age-related (AMD), results in a loss of vision in the center of the visual field due to damage to the central region of the retina, called the macula. Specifically, the macula is an oval-shaped spot near the center of the retina at the back of the eye, with a diameter of about 1.5 mm. Toward the center of the macula is the fovea, a small pit that contains the largest concentration of cone cells in the eye and is thus responsible for central, high resolution vision. Consequently, degeneration of the macula can result in the loss of abilities that require sharp central vision, such as reading.

Treatment for these and other conditions often includes the introduction of therapeutically effective agents, including but not limited to drugs, into the vitreous chamber of the eye. In the prior art, the most common way to introduce such agents is by injecting them directly into the eye, and in many cases the course of treatment requires repeated injections. This can put the patient at risk of complications such as infection, endophthalmitis, high intraocular pressure, glaucoma, cataract, retinal detachment and bleeding, and poor wound-healing. Recently, the use of ocular shunts is becoming more and more common. Most commonly, the shunt may be implanted under a flap cut into the sclera, with a flow tube inserted into the anterior chamber of the eye. This may allow the aqueous humor to drain, preventing intraocular pressure (IOP) from rising too high. The humor typically drains into a plate that is implanted underneath the flap in the sclera to form a blister-like chamber called a bleb. A common and potentially catastrophic early postoperative complication is hypotony, i.e., excessive leakage of aqueous humor resulting in low intraocular pressure. Extreme hypotony can cause a devastating deflation of the eyeball. Thus, common methods of treatment are fraught with challenges. The herein disclosed apparatus, systems, and methods can be used to address some of those challenges.

Figure 2A:
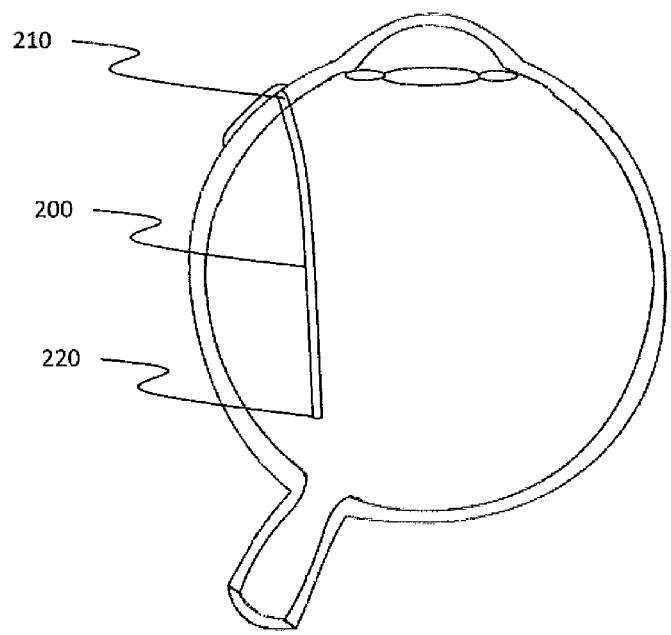
FIG. 2A is an exemplary embodiment of a shunt in accordance with the disclosure.

Referring now to FIG. 2A, a shunt 200 may be implanted through the sclera of the eye and on into the vitreal chamber. When implanted, the shunt has a proximal end 210 protruding through the surface of the sclera, and a distal end 220 within the vitreal chamber. Preferably, the shunt may be inserted into the eye in a manner to position the distal end near to the back of the eye that is being treated. The shunt may provide access to the interior of the eye for a plurality of applications of pharmaceutical agents to the back of the eye while mitigating potential complications from repeated intraocular injections. In an embodiment of the present invention, at least a portion of the outer and/or inner surface(s) of the shunt, particularly where it passes through the sclera, may be coated with one or more agents, such as silver ions, anti-proliferative drug/polymer coatings, and/or antibiotics, to mitigate the possibility of trans-scleral infection and/or inflammation.

In alternative arrangements, the distal end of a shunt tube may be introduced into the anterior chamber instead of into the vitreal chamber. If so, miotic agents such as pilocarpine may also be delivered with the shunt to increase the outflow of aqueous humor to alleviate high IOP.

Figure 2B:
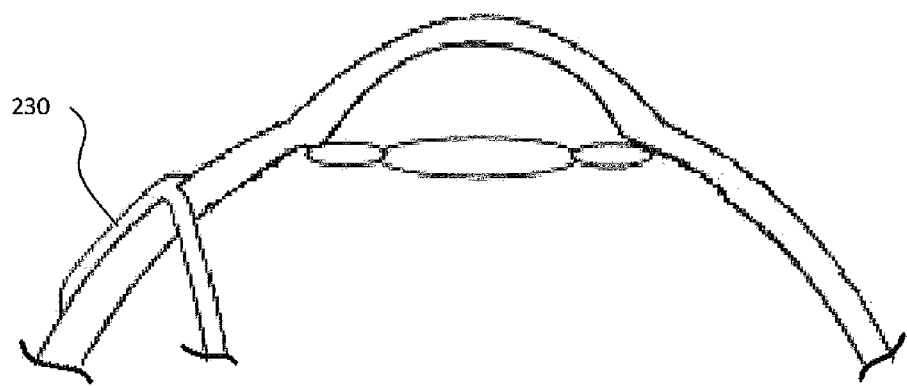
FIG. 2B illustrates in greater detail the front portion of FIG. 2A.

As shown in FIG. 2B, in an embodiment of the present invention the shunt may comprise a hydrogel portion 230 that contains one or more pharmaceutical agents to be introduced into the eye. The hydrogel portion may be formed into an appliance that is placed at the surface of the sclera in the intraorbital space, or alternatively, under a flap that is surgically cut into the sclera. The appliance may be formed with one or more edges or tabs that contain holes by which it can be sutured into place. Preferably, the hydrogel may be formed of a non-degradable biomedical material having well accepted biocompatibility. As such, there are a plurality of acceptable hydrogel and non-hydrogel materials for use in the instant invention.

By way of non-limiting example, hydrogels having varying degrees of equilibrium water uptake (such as in a range of 5% to 500% w/w) may be synthesized by reacting combinations of monomers and macromers as discussed immediately below and by way of non-limiting example only. Monomers leading to high water content hydrogels may include acrylic monomers, hydroxyethylmethacrylate (HEMA), vinylalcohol, Methacryloyl phosphorylcholine (MPC), Acrylamide (Am), di-methyl aminoethyl methacrylate (DMAEMA), and acrylic acid (AA). Macromers leading to high water content hydrogels may include sodium polyacrylate, polyurethane, PEG, hydrophilic segmented polyurethane urea, polyether block amide, hydrophilic polyamide, agarose, carboxymethyl cellulose, alginate, chitosan, hyaluronan, and Glycosaminoglycan (GAG) such as heparan sulfate.

Correspondingly, and also by way of non-limiting example only, monomers leading to minimal to low water content polymeric structures may include methyl methacrylate monomer (MMA) and perfluorinated mononers. Macromers leading to minimal to low water content polymeric structures may include polyurethane, polyurethane urea, polypropylene copolymers, polyether block amide, polyamide, thiol-ene polymers, and Diels-Alder polymers.

Figure 2C:
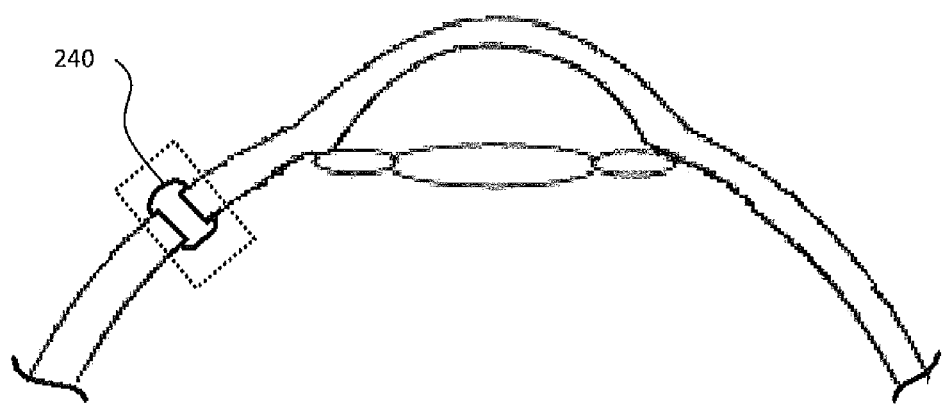
FIGS. 2C and 2D illustrate various exemplary embodiments of shunts in accordance with the disclosure.

In another embodiment illustrated in FIG. 2C, the shunt may provide a safe portal for a plurality of injections, and may not extend far past either the interior or exterior surface of the eye wall. As shown, the shunt may include a self-healing septum 240 that may act as a partition wall to provide physical separation between the intraocular and intraorbital spaces, while maintaining a safe conduit for repeated needle insertion. The septum may be disposed at any convenient location at or near the sclera. In certain embodiments, the outer and/or inner surface(s) of the shunt may be coated with one or more agents, such as silver ions and/or antibiotics, to mitigate the possibility of trans-scleral infection. The septum is preferably constructed of a silicone elastomer, although other materials may be used. In addition, the shunt may be formed of or include polymers or polymer composites with added healing agents, catalysts, or reactive agents that may provide enhanced mechanical performance and resistance to degradation and oxidation. Healing of polymer materials can also be induced by applying heat, ultraviolet light (UV), or an electric field to the shunt. For example, heating may encourage further polymerization to repair a damaged shunt and/or UV light may initiate free radical polymerization to repair a damaged shunt. Alternatively or in addition, silicone elastomers may be incorporated with polymerization initiators that yield silanolate end groups capable of living type reactions via heating.

Unwanted increase in intraocular pressure (IOP) may arise due to repeated intraocular injections. This can be treated or prevented with one or more of prostaglandin analogs, beta blockers, alpha agonists, and carbonic anhydrase inhibitors. Anti-inflammatory and immunosuppressant agents such as dexamethasone or other corticosteroids or corticosteroid derivatives, and mammalian Target Of Rapamycin (mTOR) inhibitors may serve to treat multiple eye diseases such as uveitis. Further, antibiotics such as besifloxacin, ciprofloxacin, moxifloxacin, azithromycin, and the like may also be included in treatments to prevent microbiologic growth due to repeated intraocular injections.

Figure 2D:
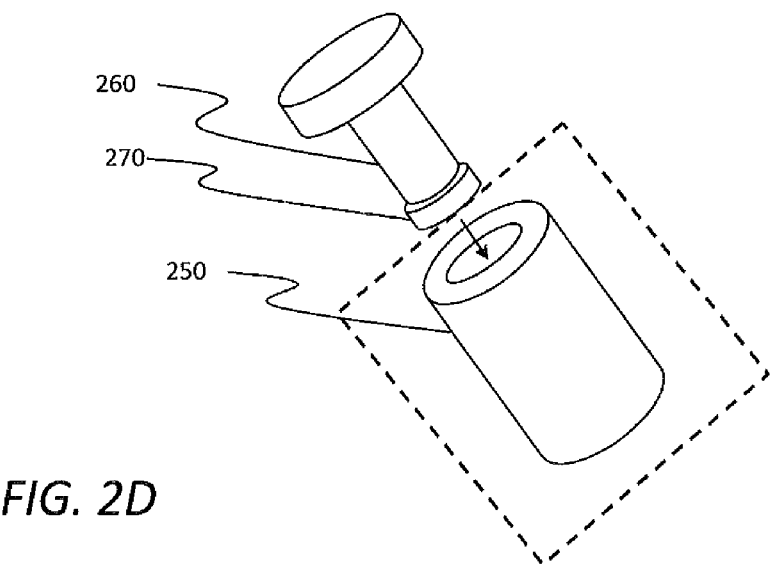

In an alternative embodiment illustrated in FIG. 2D, the shunt 250 may be re-sealed with a biocompatible polymer plug 260 after each injection. The plug may be impregnated with one or more timed-release therapeutic agents before being inserted within the shunt tube. Timed-release therapeutic agents may include, for example, prostaglandin analogs (e.g. Xalatan, Lumigan, Travatan Z), Beta blockers (e.g. timolol), alpha agonists (e.g. Alphagan P, iopidine), carbonic anhydrase inhibitors, or combinations of these. Corticosteroids, dexamethasone, mTOR inhibitors, paclitaxel, Eylea (a Vascular Endothelial Growth Factor (VEGF) receptor), anti-VEGF antibodies, Avastin, and Lucentis can also be applied. In embodiments, the plug may be used in conjunction with a septum of self healing polymer biomaterial located in the interior of the shunt. The plug may include a structure 270 that fits into a homologous structure in the shunt 250, which together serve to secure the plug within the shunt and prevent its inadvertent removal.

In certain embodiments, at least a portion of the shunt may be formed by extrusion from a thermoplastic polymer in a relative biocompatible solvent such as N-methylpyrrolidone or a solvent/water based mixture. One method of installing a shunt is to use a small gauge needle to create a track through the sclera into which the shunt is inserted. Alternatively, a laser may be used to create the track.

Further, in certain embodiments, the shunt may include an element built into the shunt's internal lumen to prevent over-reaching of the needle that injects the therapeutic agent, which could potentially damage ocular components such as the lens or the retina. One such element is an internal lumen of gradually decreasing diameter, ending in a diameter that is a smaller gauge than that of a select ophthalmic injection needle, or of a range of commonly used needles. Alternatively, a shunt lumen may be designed to be used in conjunction with a homologous or otherwise compatibly designed injection needle, which together implement a stopper element to prevent accidental damage to internal eye structures.

Additionally, in an embodiment, a coating of antibiotic drug may be applied to the shunt by spray coating, direct fluid application, and/or dip coating. The coating may also be ablated on the outer surface of the shunt, or on both outer and internal surfaces. The coating may include extracellular matrix materials such as biocompatible polymers or hydrogels, to provide improved adhesion and stability of the shunt at the trans-scleral implant site. Such materials may be naturally derived, or may be synthetic. For example, naturally derived materials may include alginate, collagen, and the like. Synthetic materials may include poly(vinylidene fluoride-co-hexafluoropropene) (PVDF-HFP), other fluorinated polymers, crosslinked polyethylene glycol, polylactide-co-glycolide, and the like.

In embodiments, sustained therapeutic agent delivery may be achieved through use of a plug impregnated with one or more time release agents. For relatively rapid release (e.g., in the range of a short portion of one day to several days) a water soluble excipient, such as polyvinylpyrrolidone (PVP) or a cellulosic, may be used to form the plug. For sustained release over a period of time lasting from a few days to several months, such as for a small molecule drug, the plug may be formed from or using hydrophobic polymers. This type of plug can include materials such as poly-DL-lactide (PDLLA), polyvinylidenefluoride-co-hexafluoropropylene (PVDF-HFP), polylactic-co-glycolic acid (PLGA), PCL, poly(ethylene-glycol-b-(DL-lactic acid-co-glycolic acid)-b-ethylene glycol (PEG-PLGA PEG), and PLGA-PEGS may be utilized as the matrix polymer. For larger molecular weight biologics, a hydrogel type matrix such as crosslinked PVP, polyethylene glycol (PEG), or biopolymers may be utilized. In embodiments, the hydrogel may be delivered as a liquid, to then gel in situ within the shunt. The shunt may also be formed to provide a sustained outflow of drug solution over time.

In embodiments, the shunt can be designed to be osmotic and swell when hydrated, and to release the pharmaceutical agent in a sustained manner over time. A pressure sensitive design may also be used to allow for fluid outflow, for example, in the case when intraocular pressure is high, to thereby alleviate high IOP.

The shunt may also incorporate a plurality of flow-through conduits, each conduit serving its own distinct purpose. For example, a dual conduit configuration may be used, wherein one conduit is adapted to receive repeated injections using fine gauge needles, while the other conduit allows for fluid outflow as necessary during injection, and/or to alleviate subsequent high IOP complications. Other numbers and combinations of conduits may be incorporated into a shunt to provide any desired combination of shunt capabilities, which may be based on, by way of non-limiting example, drug particle size, required or desired volume, or the like.

Figure 3A:
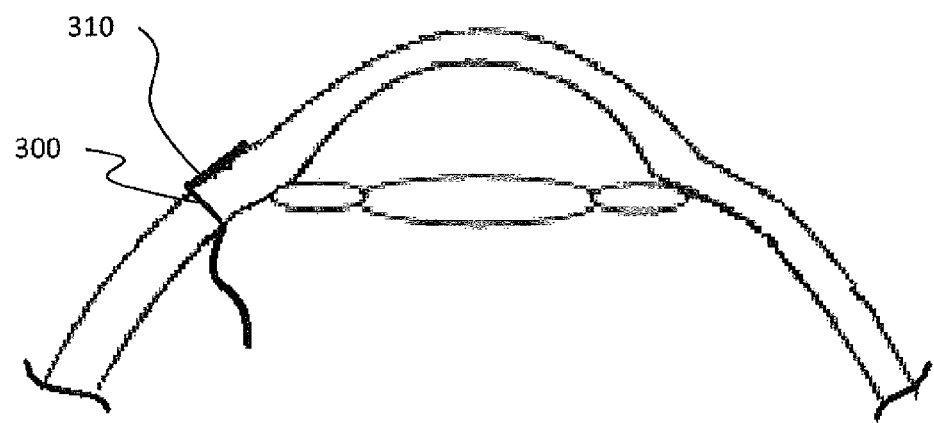
FIGS. 3A, 3B, and 3C illustrate other disclosed exemplary embodiments.

Referring now to FIG. 3A, another form of re-loadable, trans-scleral insert is illustrated for sustained release of anti-angiogenic drug in the posterior segment of the eye. Here, a swell loadable hydrogel insert 300 may have a micron scale tab 310 (shown much exaggerated for visibility) which juts out of the sclera as an external mass transport channel when the shunt is implanted. A therapeutic agent may be impregnated into the hydrogel. The agent may be or include therapeutic cells, such as stem cells. Agent-loaded nanoparticles (Np) can also, or alternatively, be impregnated into the gel.

Figure 3B:
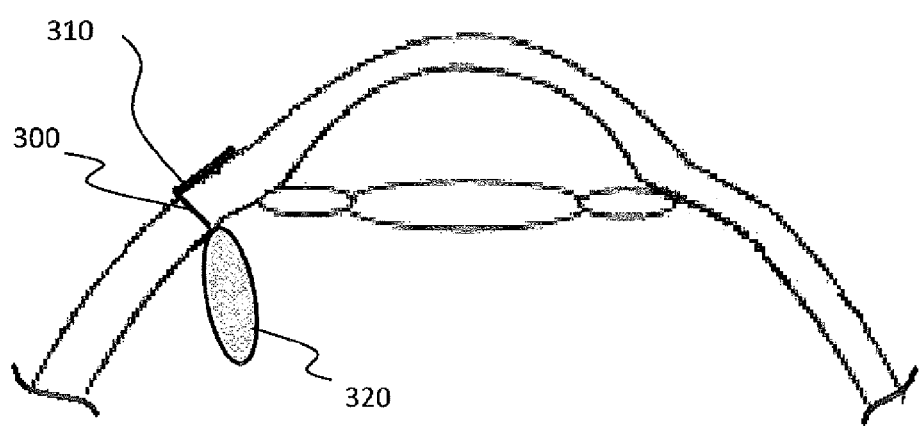

As shown in FIG. 3B, the shunt may be used as, or in conjunction with, a drug depot 320 for sustained drug release. The depot 320 may be disposed in the vitreous chamber as shown, or can be disposed on the surface of the sclera or surgically placed under a scleral flap. Therapeutic agents that can be loaded into the depot and released over time can include paclitaxel, anti-VEGF antibodies, and other anti-VEGF biologics for the treatment of retinal eye diseases such as wet age-related macular degeneration, diabetic retinopathy, and macular edema, among others. Therapeutic agents may also be delivered to treat conditions that might otherwise arise after tube-shunt surgery, such as to reduce scar tissue and/or to prevent infection.

In an exemplary operation, at the end of a round of therapeutic agent delivery near the exhaustion of the agent reservoir, a fresh agent solution may be added to the reservoir, for example, by the application of eyedrops or an eyewash. The agent may wick through the hydrogel tab, through the trans-scleral pathway, and on into the intravitreal space, where it may be conveyed to the vitreous humor.

In an exemplary embodiment, the hydrogel insert may be or comprise a nanotube or other strand with an external diameter in the range of about 100 nm to about 2 µm. Alternatively, the implant may be or comprise a thin film having a thickness in the range of about 500 nm to about 2 µm. In either case, the proximal end of the strand or film (hereinafter collectively "strand") creates a wicking window through the sclera, and the distal end can deliver the therapeutic agent to the vitreous humor.

Figure 3C:
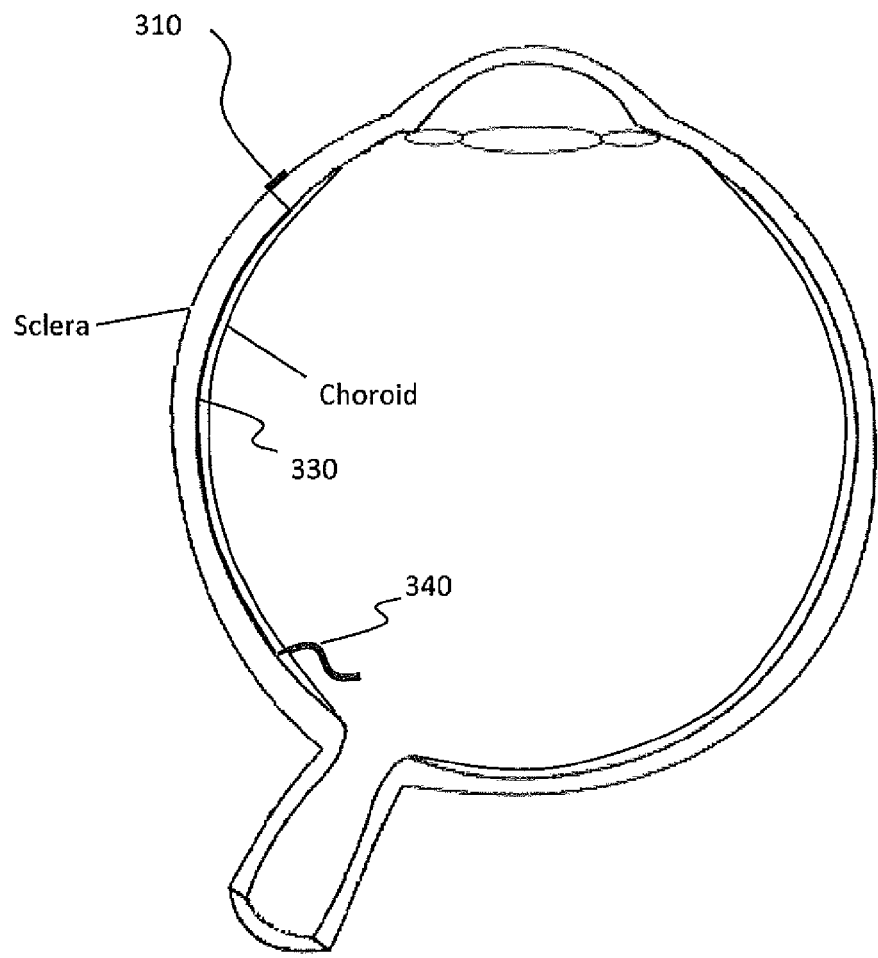

Alternatively, as shown in FIG. 3C, a swell loadable hydrogel strand 330 may be inserted between the choroid and the sclera, again with a micron scale tab 310 jutting out of the sclera at the proximal end as an external mass transport channel. In such an embodiment, the distal end of the strand 340 may be placed near to the area being treated. Thereby, the choroid and sclera may hold the insert in place to provide a delivery pathway directly to the area being treated. The hydrogel insert may open into the vitreous space through a trans choroidal access, as shown. Alternatively, the insert may not open into the vitreous space. Instead, the agent can diffuse into the choroidal blood vasculature to treat the back of the eye.

In short, the insert is preferably outside the visual field upon implantation, and should remain so. Accordingly, the insert may be implanted anywhere about the posterior segment of the eye, and may be sized and shaped so as not to provide the possibility of impairment of the visual field. Moreover, in the event of failure of the insert or entry into or affect on the visual field by the insert, the insert may be removed.

A hydrogel for use with the present invention may be made of or include PEG, PVP, GAG, PAA, CMC, CPMC, HPMA hyaluronic acid, Poloxamer F127, functionalized PEG, PVA, HEMA, silicon gels, sodium alginate, PolyMPC, etc., and/or a combination of these. At the end of a round of therapeutic agent delivery and near the exhaustion of the agent supply stored in the insert or in a reservoir coupled thereto, a fresh agent solution may be simply added to the strand, for example, using eyedrops, an eyewash, or other method of recharging the storage medium. The agent may wick through the hydrogel tab and through the trans-sclera tunnel into the swell loadable insert, and/or to the distal end of the strand.

In certain embodiments, a hydrogel or polymeric insert may be reversible, and/or may be triggered to release its therapeutic agent on demand via appropriate stimuli. For example, the stimuli may be electroactive (e.g. polyaniline); pH sensitive (e.g., administration of slightly acidic eye drops), or temperature sensitive (e.g., administration of cold drops to eye). The stimuli may also be based on light sensitivity (e.g., administration of ultraviolet light, or well-aimed laser light directed at the insert), or enzyme sensitivity (e.g., administration of an enzyme to increase insert degradation and accelerate drug release). Further, an immunosuppressant and/or anti-proliferative agent such as Zotarolimus may be used to coat the shunt to mitigate certain conditions that may arise from the use of the shunt. One or more other agents may also be used in conjunction with Zotarolimus. For example, Zotarolimus plusan anti-tumor necrosis factor (anti-TNF) can be used.

In yet other embodiments, drug conjugation into macromers for sustained release via lability-controlled dissociation of the active agent from the macromeric prodrug may be utilized. Here, the drug may be conjugated, for example, into Hyaluronic acid, GAG through ester bond or anhydride bonds, or other chemically labile bonds. In such an embodiment, a macromeric prodrug may be injected intravitreally. The labile bong may release the drug over time. Alternatively, the drug may be conjugated into Vitrosin (collagen in IVT) and injected intravitreally. The drug can be conjugated into these polymers as a pendant group, or in endgroups, for example, PEG, PVP, GAG, PAA, CMC, CPMC, HPMA hyaluronic acid, PolyMPC, etc/, or a combination of these. The drug can also be conjugated into dynamers and injected Intravitreally. In this way, drug release may depend on H-bonding strength.

In certain embodiments, the drug may be conjugated into Hyaluronic acid, GAG through ester bond or anhydride bonds or other chemically labile bonds. The macromeric prodrug may be injected intravitreally, and the labile bong may release the drug over time. Alternatively the drug may be conjugated into Vitrosin (collagen in IVT) and injected intravitreally. The drug may be conjugated into these polymer as a pendant group or endgroups, such as PEG, PVP, GAG, PAA, CMC, CPMC, HPMA hyaluronic acid, PolyMPC etc and/or a combination of these.

In embodiments, conjugated bonds may release a drug in response to exposure to fluorescent light. Thereby, drug delivery may be controlled on demand. The macromeric prodrug may again be delivered intravitreally, and the labile bong may release the drug on demand using a Fluorescent trigger. Alternatively the drug may be conjugated into Vitrosin (collagen in IVT), and/or into dynamers, and delivered intravitreally. Drug release may still depend on H-bonding strength and use of a fluorescent trigger.

In embodiments, conjugated bonds may be or include physical bonds such as H-bonding, electrostatic interaction, Hydrophobic interaction, Au—S bonds, or the like. This may enable sustained release drug delivery without covalent chemical bond formation. The physical complexation of an active agent with an excipient may not change any cheniocal bonds in the drug structure, and hence may not be considered a new entity. The drug can be complexed with Hyaluronic acid and/or other GAG and then injected Intravitreally. Either small molecular weight (MW) drugs or biologics, or both, can be included in this configuaration. In addition to complexation with polymers already mentioned, oligomeric and monomeric entities may also be used for physical complexation with the drug, such as Glycerol, Mannitol, Mannose-6-phosphate, and the like.

In an embodiment of the present invention a drug coated angioplasty balloon (not shown) may be used to treat retinal diseases such as AMD, macular edema, and diabetic retinopathy. A drug may be conjugated into Hyaaluronic acid through an ester bond or anhydride bonds. The macromeric prodrug may be delivered intravitreally as described hereinbefore, and the labile bong may release the drug over time. Alternatively, a drug may be conjugated into Vitrosin (collagen in IVT) and delivered intravitreally. In embodiments, a drug may be conjugated into such polymers as a pendant group or as end-groups, for example, PEG, PVP, GAG, PAA, CMC, CPMC, HPMA hyaluronic acid, PolyMPC, or the like, and/or a combination of these. A drug may also be conjugated into dynamers and delivered intravitreally, and drug release may depend on H-bonding strength as before. Anti-angiogenic and neuroprotective drugs can include, for example, ABT-869 (multi-targeted kinase inhibitor), Aurora Kinase inhibitor (ABT-348 and 993), JAK Kinase (ABT-317), TSP-1 (ABT-898, 567), 81 P1 (ABT-413), Zotarolimus, BcI-2 (ABT-199), BcI-2 BU, Cal pain, RGMa antibody, DLL-4 Ab, PGDF antibodies, pKC small molecule inhibitors, DVD-Ig molecules combining VEGF, DLL-4, PGDF, EGFR Ab, and RGMa binding domains, and/or combinations of these.

In certain embodiments, a drug may be conjugated into hyaaluronic acid, but through bonds that may release drug in response to a fluorescent light trigger to enable drug delivery on demand. A macromeric prodrug, for example, may be delivered intravitreally, and the labile bong may release the drug on demand by use of the fluorescent trigger. Alternatively, a drug may be conjugated into Vitrosin (collagen in IVT) and delivered intravitreally and/or conjugated into the following polymers as a pendant group or as end-groups: PEG, PVP, GAG, PAA, CMC, CPMC, HPMA hyaluronic acid, PolyMPC, etc., and/or a combination of these. The drug may also be conjugated into dynamers and delivered intravitreally. Once again, drug release may depend on the H-bonding strength and fluorescent trigger.

In embodiments, sustained release of an anti-angiogenic drug may be performed in the posterior segment of the eye using an implanted device that may not be particulate. A micron-size absorbable polymeric monolithic implant (such as a ribbon, mat, stent, disc, cylinder, etc.) may be loaded with an anti-angiogenic drug. The implant surface may be coated as described previously. The implant may be deployed either by intravitreal delivery in a buffer, or in a viscous, lubricious vehicle such as haluronic acid. Such a drug may be impregnated into a monolithic structure (such as an absorbable stent) or coated on the surface (the structure may incorporate pores to hold the drug). Thereby, the quantity of drug and the rate of drug release may be tailored by adapting the size and quantity of pores to suit the particular application. Illustratively, the structure may be embodied as a stent, which may be placed in the back of the eye away from the field of vision, and apposed at the bottom of the retinal wall. Similarly, the surface of the stent can be coated with swellable hydrophilic polymer such as PEG, PVP, MPC, etc. so that little to no trauma is induced to the retina.

In certain alternative embodiments, an absorbable Np loaded anti-angiogenic drug may be embedded in a slowly dissolvable strip. One or more such strips may be injected into intravitreal space. An Np embedded strips may be placed in multiple locations in IVT. Such a dissolvable strip may be made of or comprise PEG, PVP, GAG, PAA, CMC, CPMC, HPMA hyaluronic acid, PolyMPC, etc., and/or a combination of these. The strip may be blended with hydrophobic excipient such as stearate, palmitate, or poly glycerol sebacate. Thereby, tailored and controlled dissolution of therapeutic agents loaded into the strip may be enabled. In embodiments, an agent may also be loaded in the strip for a bolus initial release. For example, Np may be impregnated into the strip as sub populations based on size and shape. This may also modulate drug release rate. In such embodiments, the strip may be blended with a hydrophobic excipient such as stearate, palmitate, or poly glycerol sebacate. This may enable tailoring controlled dissolution of the strip, as before. Zotarolimus may also be used as an active agent. As may be appreciated by those skilled in the art, multiple drugs may also be used. For example, Zotarolimus may be used in conjunction with anti-TNF.

Figure 4A:
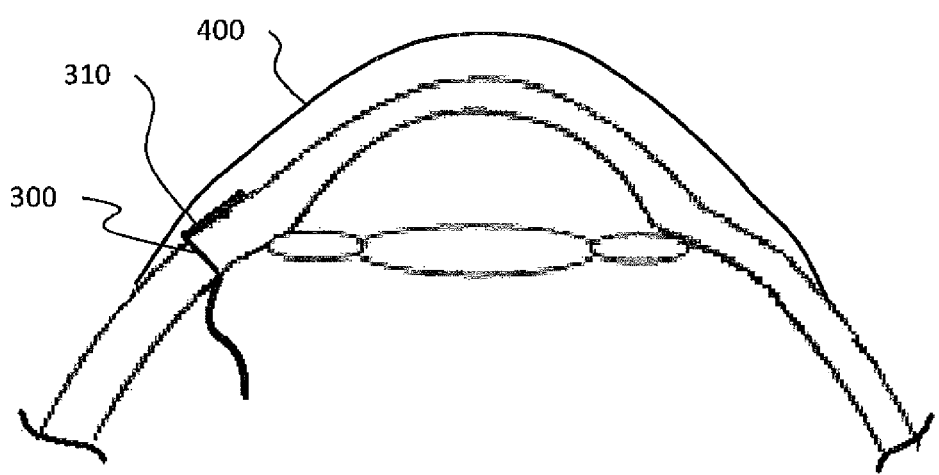
FIG. 4A illustrates an agent-loadable contact lens used in conjunction with a trans-sclera portal.

Turning now to FIG. 4A, an illustration of an embodiment of a drug-loadable contact lens is shown. The lens 400 may function as an ordinary contact lens, except that it is made of or includes a portion made of so-called block-copolymers. In a block-copolymer, the copolymer is microphase separated to form a periodic nanostructure that may be used as a depot to store the therapeutic agent. The nanostructure may provide storage regions that are small enough to not scatter light, and have miscibility with the agent, thereby providing for a controlled release of the agent.

Figure 4B:
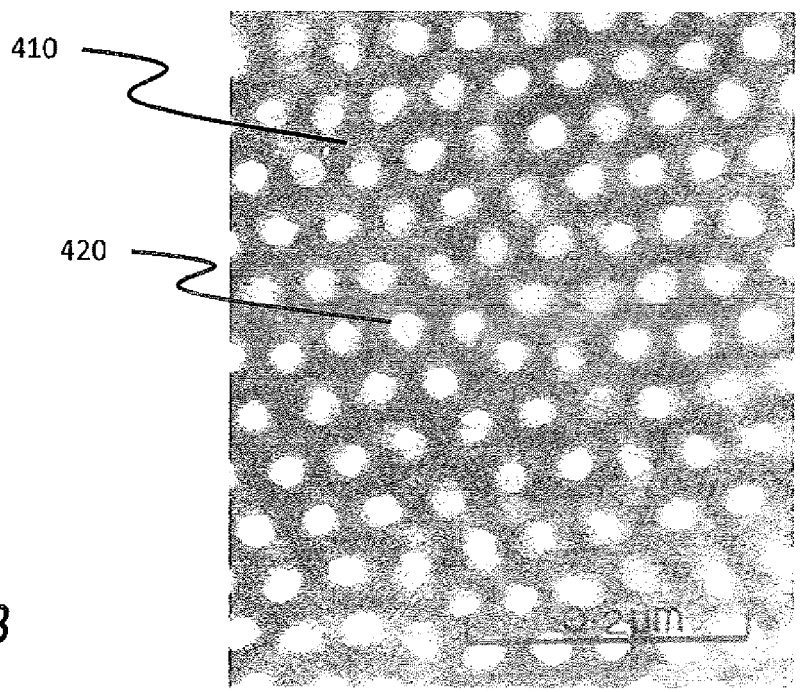
FIG. 4B is a micrograph of a portion of the contact lens of FIG. 4A.

FIG. 4B illustrates an exemplary block copolymer nanostructure comprising a matrix 410 in which microphase separated regions 420 may be embedded. The matrix, which makes up most of the lens, may be or comprise a conventional hydrogel such as HEMA or a silicone material. The regions where the drug is stored may be of a more hydrophobic nature, such as PEA, polymers made through metathesis polymerizations, and controlled free radical polymerization, to provide very well defined block sizes. Used in conjunction with a shunt comprising one or more strands having a micron scale tab protruding from the surface of the sclera, the contact lens may serve as a repository of therapeutic agent that is absorbed over time by the strand(s), and wicks through the sclera into the vitreal chamber, or between the sclera and choroid to the treatment site.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. An implantable trans-sclera portal for repeated injection of ophthalmic pharmaceutical treatments into an eye, comprising:
   a shunt having an inner diameter and an outer diameter, wherein the shunt is osmotic and a distance between the inner diameter and the outer diameter increases when the shunt is hydrated;
   a first internal lumen within the shunt that provides a first conduit for repeated injections into the eye, the first internal lumen having a first diameter at a first end proximate to the outside of the eye, and a second diameter at a second end open to the inside of the eye, wherein the first diameter is greater than the second diameter;
   a partition wall within the internal lumen that is arranged, upon implantation of the shunt into the eye, to provide separation between the inside and outside of the eye; and
   at least one of a healing agent, a catalyst, and a reactive agent included with the partition wall.

2. The trans-sclera portal of claim 1, wherein at least a portion of the shunt is formed of a silicon elastomer.

3. The trans-sclera portal of claim 1, wherein a surface of the shunt is coated with a therapeutic agent effective to prevent trans-scleral infection.

4. The trans-sclera portal of claim 3, wherein the therapeutic agent comprises silver ions or an antibiotic.

5. The trans-sclera portal of claim 1, wherein the partition wall comprises a septum.

6. The trans-sclera portal of claim 5, wherein the septum is self-healing.

7. The trans-sclera portal of claim 1, wherein the partition wall comprises a biocompatible polymer plug that re-seals after each injection.

8. The trans-sclera portal of claim 1, wherein the shunt is configured to provide the injected pharmaceutical to a posterior segment of the eye.

9. The trans-sclera portal of claim 1, wherein the at least one of the healing agent, the catalyst, and the reactive agent provide enhanced mechanical performance and resistance to degradation and oxidation.

10. The trans-sclera portal of claim 1, wherein the second diameter is smaller than a gauge of a needle used to perform the repeated injections.

11. The trans-sclera portal of claim 1, further comprising:
    a biocompatible polymer plug having a complimentary shape to the first internal lumen.

12. The trans-sclera portal of claim 1, further comprising:
    a second internal lumen within the shunt that provides a second conduit for an outflow of liquids during an injection.

13. A method of treating a patient's eye, comprising:
    surgically implanting in the eye a shunt, the shunt comprising:
       an outer diameter and an inner diameter, wherein a distance between the inner diameter and the outer diameter increases when the shunt is hydrated,
       a first internal lumen within the shunt, the first internal lumen having a first diameter at a first end proximate to the outside of the eye, and a second diameter that is open at a second end proximate to the inside of the eye, wherein the first diameter is greater than the second diameter, and
       a partition wall within the internal lumen that provides separation between the inside and outside of the eye;
    injecting a dose of therapeutic agent into the eye by inserting a needle through the partition wall within the first lumen and into an interior of the eye and removing the needle; and
    thereafter, injecting a second dose of therapeutic agent into the eye by inserting a needle through the partition wall within the first lumen and into the interior of the eye and removing the needle.

14. The method of claim 13, wherein the partition wall comprises a resealable biocompatible polymer plug, further comprising re-sealing the plug after each injection.

15. The method of claim 14, wherein the partition wall comprises a septum.

16. The method of claim 15, wherein the septum is self-healing.

17. The method of claim 13, wherein the shunt is configured to provide the injected therapeutic agent to a posterior segment of the eye.

18. The method of claim 13, further comprising coating a surface of the shunt with a therapeutic agent effective to prevent trans-scleral infection prior to the surgical implantation.

19. The method of claim 18, wherein the agent comprises silver ions or an antibiotic.

20. The method of claim 13, wherein the second diameter is smaller than a gauge of the needle.

21. The method of claim 13, wherein the shunt further comprises:
    a biocompatible polymer plug having a complimentary shape to the first internal lumen.

22. The method of claim 13, wherein the lumen further includes a second internal lumen within the shunt.

* * * * *